US010869618B2

(12) United States Patent
Quintel

(10) Patent No.: US 10,869,618 B2
(45) Date of Patent: Dec. 22, 2020

(54) DIAGNOSTIC MEASUREMENT DEVICES AND METHODS

(71) Applicant: Thomas William Quintel, Charleston, SC (US)

(72) Inventor: Thomas William Quintel, Charleston, SC (US)

(73) Assignee: Thomas William Quintel, Charleston, SC (US)

( * ) Notice: Subject to any disclaimer, the term of this patent is extended or adjusted under 35 U.S.C. 154(b) by 809 days.

(21) Appl. No.: 15/098,476

(22) Filed: Apr. 14, 2016

(65) Prior Publication Data

US 2017/0296105 A1 Oct. 19, 2017

(51) Int. Cl.
*A61B 5/11* (2006.01)
*A61B 5/00* (2006.01)

(52) U.S. Cl.
CPC .......... *A61B 5/1121* (2013.01); *A61B 5/6825* (2013.01); *A61B 5/6831* (2013.01); *A61B 2503/10* (2013.01)

(58) Field of Classification Search
None
See application file for complete search history.

(56) References Cited

U.S. PATENT DOCUMENTS

| 405,128 | A | * | 6/1889 | Stockburger | ....... A63B 21/0724 482/106 |
| 1,468,688 | A | * | 9/1923 | Elliott | ..................... G01C 9/12 33/391 |
| 2,565,381 | A | | 8/1951 | Leighton | |
| 2,598,552 | A | | 5/1952 | Jansen | |
| 4,102,055 | A | | 7/1978 | Volk, Jr. | |
| 4,257,591 | A | * | 3/1981 | Evans, Sr. | .......... A63B 21/0004 482/91 |
| 4,846,194 | A | * | 7/1989 | Sabia | ..................... A61B 5/107 600/594 |
| 4,928,709 | A | * | 5/1990 | Allison | ................ A61B 5/1121 33/355 R |
| 5,758,658 | A | | 6/1998 | Petragallo | |
| 6,073,356 | A | | 6/2000 | Li | |
| 6,857,994 | B2 | * | 2/2005 | Yu | ....................... A63B 21/0004 482/121 |
| 7,594,286 | B2 | | 9/2009 | Williams | |
| 7,662,073 | B1 | * | 2/2010 | Baldwin | ............ A63B 21/4021 482/139 |

(Continued)

OTHER PUBLICATIONS

Audette et al. ("Validity and Between—Day Reliability of the Cervical Range of Motion (CROM) Device" Journal of Orthopaedic & Sports Physical Therapy, vol. 40, No. 5, May 2010, pp. (318-323)).*

(Continued)

*Primary Examiner* — Rene T Towa
(74) *Attorney, Agent, or Firm* — Thrive IP®; Jeremy M. Stipkala; William La Salle, III

(57) ABSTRACT

A device for measuring an angular difference in a range of motion of the arms of a patient comprises a gripping bar, a housing, and an angle-determining assembly comprising a weighted needle and a compass. When the patient raises her arms to their unassisted physiological limits, the device indicates an angle that represents the angular difference in the range of motion between the arms of the patient.

9 Claims, 11 Drawing Sheets

(56) References Cited

U.S. PATENT DOCUMENTS

| | | | |
|---|---|---|---|
| 7,942,785 B1 * | 5/2011 | Russell | A61B 5/1121 |
| | | | 482/44 |
| 8,282,579 B2 | 10/2012 | Bright et al. | |
| 8,818,751 B2 | 8/2014 | Van Acht et al. | |
| 8,888,665 B2 * | 11/2014 | Pfitzer | A63B 21/0602 |
| | | | 482/104 |
| 8,898,917 B1 | 12/2014 | Noubarian | |
| 2007/0027005 A1 * | 2/2007 | Hetrick | A63B 21/0023 |
| | | | 482/91 |
| 2012/0309596 A1 * | 12/2012 | Kennedy | A63B 21/0602 |
| | | | 482/93 |
| 2013/0116096 A1 * | 5/2013 | Mikulski | A63B 21/0724 |
| | | | 482/106 |

OTHER PUBLICATIONS

The editors of Encyclopaedia Britannica ("Compass", Encyclopaedia Britannica, inc., Nov. 22, 2016).*

* cited by examiner

© 2016 Thomas William Quintel

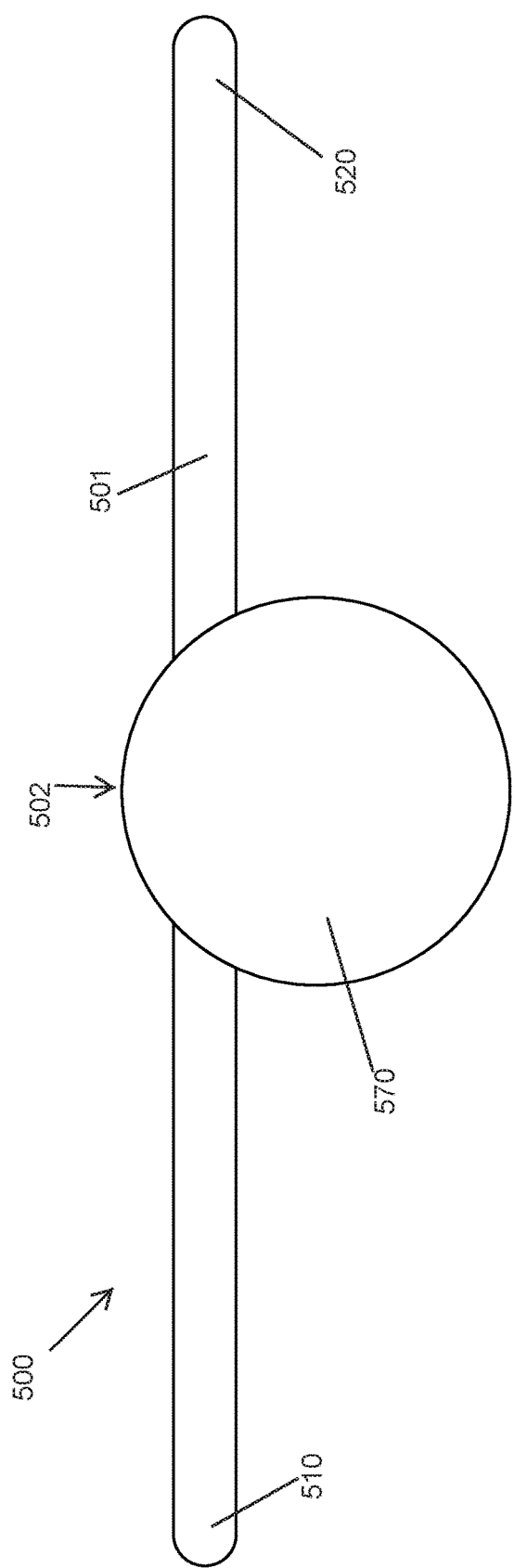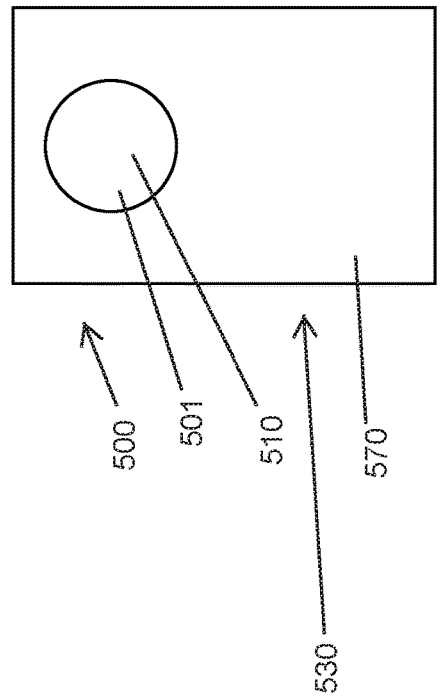

© 2016 Thomas William Quintel

DIAGNOSTIC MEASUREMENT DEVICES AND METHODS

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF INVENTION

This invention relates to diagnosing and treating injury or disease in a patient in need thereof, and methods and devices therefor.

BACKGROUND OF THE INVENTION

Injury or disease often limits the range of motion of a person's limbs. Sometimes, the presence of an injury or disease can be revealed by such a limit in the range of motion. Measuring the range of motion and determining the presence of injury or disease can be difficult, given the variability in body shape, age, fitness level, and other factors. For example, a typical healthy 20-year-old can raise her arms far higher than a typical healthy 80-year-old. Similarly, detecting differences in the ranges of motion between two limbs on the same person also can be difficult. Conventionally, a goniometer measures the angle to which a person can raise her arm. However, proper placement, measurement, and reading the goniometer may not be straightforward for all persons. In addition, comparing the range of motion of an injured or diseased limb to that of a healthy limb requires multiple measurements, unnecessarily inserting uncertainty into diagnosis and treatment.

An easy way of measuring an angular difference in the range of motion between two arms of a patient is needed. Methods of treatment are also needed.

SUMMARY OF THE INVENTION

Unexpectedly, Applicant has invented methods and devices for measuring angular differences in ranges of motion of the arms of patients in need thereof, and diagnosing injury or disease thereby. Accordingly, some embodiments of the present invention relate to methods of diagnosing an injury or disease in a patient in need thereof, comprising: measuring an angular difference in a range of motion in the arms of the patient, thereby diagnosing the injury or disease.

Further embodiments of the present invention provide devices for measuring an angular difference in a range of motion of the arms of a patient in need thereof, the devices each comprising:
a gripping bar comprising a left end, a right end, and a midpoint equidistant between the left end and the right end;
a housing attached to the gripping bar at the midpoint, and an angle-determining assembly supported by the housing, the assembly comprising a weighted needle configured to point vertically when subjected to the force of gravity; a base affixed to the housing, wherein the weighted needle is rotatably attached to the base by an axle; and a compass configured to indicate with the weighted needle an angle between an absolute vertical axis and a vertical axis of the housing perpendicular to the gripping bar.

Still other embodiments relate to methods of measuring an angular difference in a range of motion of the arms of a patient in need thereof, comprising:
obtaining any suitable device such as a device described herein;
having the patient grip the left end in the patient's left hand and the right end in the patient's right hand;
having the patient raise both arms to both arms' unassisted physiological limits; and
observing on the compass with the weighted needle the angle, wherein the angle represents the angular difference in the range of motion of the arms of the patient.

Yet additional embodiments relate to methods of treating an injury or disease in a patient in need thereof, wherein the injury or disease manifests an angular difference in a range of motion of the arms of the patient, the method comprising:
obtaining the device as described herein;
having the patient grip the left end in the patient's left hand and the right end in the patient's right hand;
having the patient raise both arms to both arms' unassisted physiological limits; observing on the compass with the weighted needle the angle, wherein the angle represents the angular difference in the range of motion of the arms of the patient; and
repeating having the patient grip the device and having the patient raise both arms, for the purpose of detecting a decrease in the angular difference in the range of motion.

While the disclosure provides certain specific embodiments, the invention is not limited to those embodiments. A person of ordinary skill will appreciate from the description herein that modifications can be made to the described embodiments and therefore that the specification is broader in scope than the described embodiments. All examples are therefore non-limiting.

BRIEF DESCRIPTION OF THE DRAWINGS

FIG. 8 shows a rear elevation view of device 500.

FIG. 9 shows a left side elevation view of device 500.

DETAILED DESCRIPTION

Figure 1:
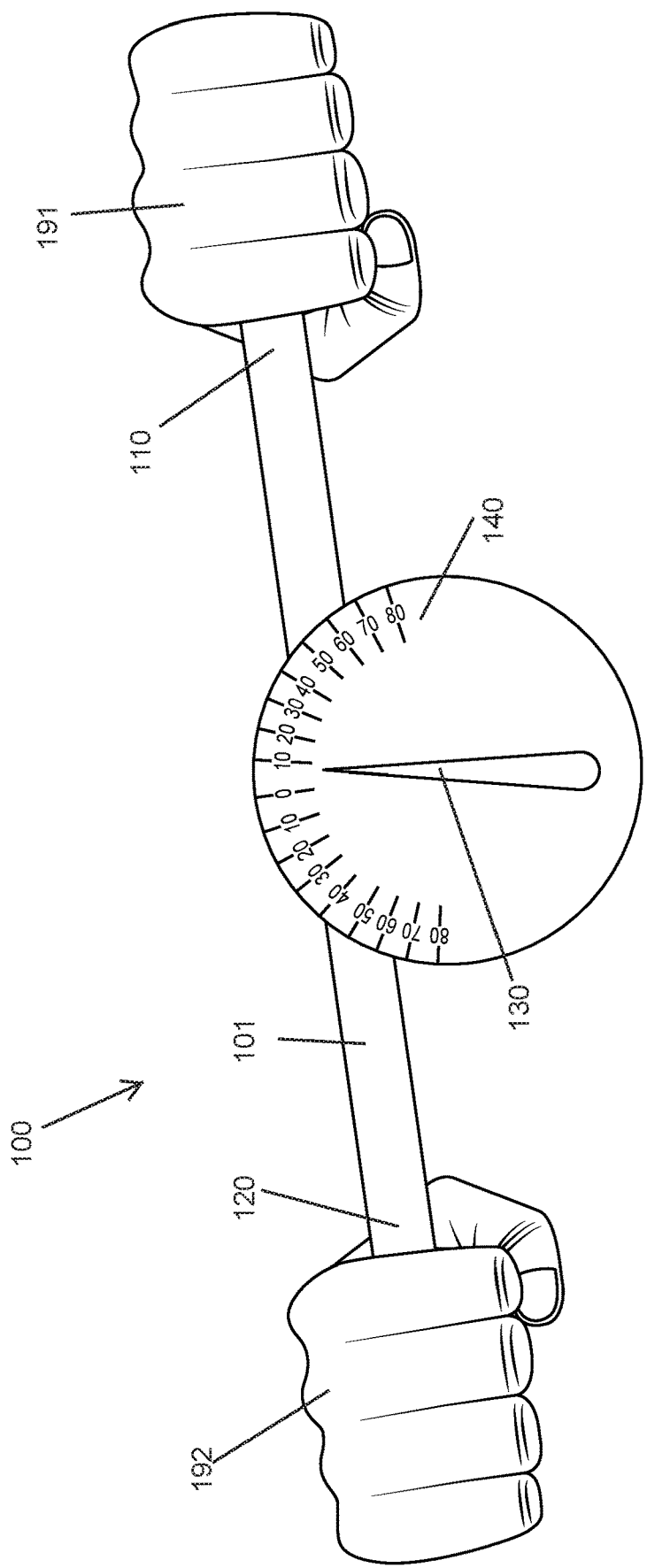
FIG. 1 provides a cartoon of one embodiment of the present invention, device 100, in use.

As required, detailed embodiments of the present invention are disclosed herein; however, it is to be understood that the disclosed embodiments are merely exemplary of the invention that may be embodied in various forms. The figures are not necessarily to scale, and some features may be exaggerated to show details of particular components. Therefore, specific structural and functional details disclosed herein are not to be interpreted as limiting, but merely as a basis for the claims and as a representative basis for teaching one skilled in the art to variously employ the present invention.

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

Where ever the phrase "for example," "such as," "including" and the like are used herein, the phrase "and without limitation" is understood to follow unless explicitly stated otherwise. Similarly "an example," "exemplary" and the like are understood to be non-limiting.

The term "substantially" allows for deviations from the descriptor that don't negatively impact the intended purpose. Descriptive terms are understood to be modified by the term "substantially" even if the word "substantially" is not explicitly recited.

The term "about" when used in connection with a numerical value refers to the actual given value, and to the approximation to such given value that would reasonably be inferred by one of ordinary skill in the art, including approximations due to the experimental and or measurement conditions for such given value.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

Any discussion of the prior art throughout the specification should in no way be considered as an admission that such prior art is widely known or forms part of common general knowledge in the field.

It is an object of the present invention to overcome or ameliorate at least one of the disadvantages of the prior art, or to provide a useful alternative.

As used herein, a "gripping bar" is any suitable apparatus for holding the device. In some cases, the gripping bar can be a single piece, and can be substantially cylindrical. In other cases, the gripping bar can comprise multiple pieces. In still other cases, the gripping bar can have any desired shape, and mirror symmetry about the midpoint is useful to evenly distribute the weight of the device about the midpoint. The "midpoint" generally means the gravitational and likely the geometric middle of the gripping bar.

In certain embodiments, a housing is attached to the gripping bar at the midpoint. The midpoint is useful in many devices so that a patient has an even burden in both arms when raising the device for diagnostic measurement. Attaching to the gripping bar at the midpoint indicates any suitable attachment. In some cases, as shown in the drawings, the gripping bar passes through the housing, thereby attaching the housing at the midpoint.

An angle-determining assembly is supported by the housing. That means the assembly is suitably attached to the housing, which in turn is attached to the gripping bar about the midpoint. The angle-determining assembly comprises a base affixed to the housing, and supports an axle which in turn supports a weighted needle. The weighted needle is free to rotate relative to the housing, and is configured to point vertically when the device is held so that the weighted needle is subjected to the force of gravity. Pointing vertically can mean that the needle points up, in some cases, or points down in other cases.

The angle-determining assembly also comprises a compass. As used herein, a "compass" is simply a display indicating an angular difference from the vertical. In some cases, that angular difference can be expressed in degrees, and "0°" is indicated on the vertical. In other cases, that angular difference is expressed in radians. The angular difference from the vertical can have any suitable range. In some instances, the range displayed on the compass ranges from 0° at the vertical to 85°, 90°, 120°, or 170° on each side. In other instances, the range displayed on the compass is positive on one side of the vertical, and negative on the other side of the vertical. In still other cases, that angular difference can be expressed in any desired manner, such as, for example, by indicating suitable ranges about the vertical that are "normal," "borderline," and "asymmetric." As can be appreciated, whether the weighted needle is configured to point up or down, the compass is arranged appropriately. The compass can be present on its own substrate, or it can be present on a watch glass, such as, for example, degree markings on a clear piece of plastic, so the weighted needle is visible proximate to the degree markings. Any suitable substrate can be used for the compass, such as, for example, metal, plastic, wood, glass, or a combination thereof.

The compass is configured with the weighted needle to indicate an angle between an absolute vertical axis and a vertical axis of the housing perpendicular to the gripping bar. An "absolute vertical axis" means an imaginary line that passes through the midpoint and through the center of the earth. A weight suspended on a string with no wind would conform to an absolute vertical axis, due to the force of gravity. A "vertical axis of the housing perpendicular to the gripping bar" indicates an imaginary line that passes through the midpoint at a reading of 0° C. on the compass.

The angle-determining assembly may further comprise a weighted pendulum supported by the axle attached to the weighted needle. The weighted pendulum aids the weighted needle in finding the vertical when subjected to the force of gravity.

The device may further comprise a watch glass affixed to the housing, configured to protect and enclose the angle-determining assembly.

Any suitable materials can be used for the devices of the present invention. In some cases, care is taken to make the device as light as possible, so that measuring an angular difference in the range of motion between two arms of a patient in need thereof is not significantly affected by the weight of the device. In other cases, weight, for example in the form of small disk weights, can be added to the device, so that the angular differences in the range of motion at different weights can be measured. In still other cases, an attachment device such as a hook, can be added to the bottom of the device, so that a variable-force apparatus such as an elastic band can be attached, and the angular difference in the range of motion under increasing force can be measured. In that case, while one end of the elastic band is attached to the device, the other end of the elastic band is suitably anchored to some stationary object, such as the floor or a suitably-designed piece of equipment. Materials suitable for the device and the components thereof include, but are not limited to, metal, plastic, wood, glass, and combinations thereof. Among metals, stainless steel and aluminum may be mentioned. Among plastics, high-impact polystyrene, high density polyethylene, other polyalkenes, polyacrylates, and vinyls such as PVC may be mentioned. Plastics may be clear, opaque, translucent, colored, or multicolored as desired.

The gripping bar can be of any suitable dimensions. In some cases, the gripping bar has a circumference that is comfortable for the human hand to grip. In other cases, the gripping bar can have removable grips of varying dimensions, so that the device can be used sometimes for children, and other times for adults with larger hands. Some embodiments of the present invention provide a gripping bar that is at least one foot long. Other embodiments of the present invention provide a gripping bar that is no more than three feet long. Still other embodiments provide a gripping bar that is adjustable in its length. It is desirable, in some cases, to provide a device that allows a patient to grasp the device with her hands at about shoulder width apart. In other cases, it is desirable to have the patient grip the device with the hands closer together, or further apart, relative to shoulder width. Accordingly, some devices of the present invention provide a gripping bar comprising at least one mechanism for adjusting the length of the gripping bar. Any suitable mechanism can be used. One suitable mechanism comprises a spring-loaded button on a first portion of the gripping bar, and a series of holes on a second portion of the gripping bar slidably mounted on the first portion, the series of holes positioned so that the spring-loaded button can selectively engages any one hole in the series of holes, thereby adjusting the length of the gripping bar. Other devices provide a gripping bar comprising a central portion comprising the midpoint and the housing attached at the midpoint, further comprising a left side opposite a right side about the midpoint, a left spring-loaded button on the left side and a right spring-loaded button on the right side;

a left hand grip comprising the left end and a left-side series of holes, the left hand grip being slidably mounted on the left side of the central portion so that the left spring-loaded button selectively engages any hole in the left-side series of holes to adjust the length of the gripping bar; and a right hand grip comprising the right end and a right-side series of holes, the right hand grip being slidably mounted on the right side of the central portion so that the right spring-loaded button selectively engages any hole in the right-side series of holes to adjust the length of the gripping bar.

Sometimes, an elderly or injured patient cannot adequately grip the devices of the present invention. Accordingly, certain embodiments of the present invention provide a device wherein the gripping bar further comprises, at the left end and the right end, one or more substantially similar gripping aids. "Substantially similar" gripping aids have approximately the same weight. If a handlebar grip is used at the left end, then a handlebar grip is used at the right end, for example. Any suitable gripping aids can be used. In some cases, gripping aids are chosen from foam grips, handlebar grips, and straps. Securing a strap around the hand of the patient can use any suitable mechanism. A strap may form a simple loop, and care should be taken so that a loop on the left side of the device is substantially the same as a loop on the right-hand side, so that the use of the loops does not introduce an artificial angular difference. Snaps, buttons, quick-release clips, and hook-and-loop attachments known as Velcro® also can be employed, alone or in combination.

Any suitable methods can be used to manufacture the devices of the present invention. In some cases, one or more of the gripping bar, housing, base, weighted needle, pendulum, and optionally the watch glass can be molded, cut, cast, or milled, as individual pieces or as a combination of two or more of those items as a single piece, as appropriate.

Methods for measuring an angular difference in a range of motion of the arms of a patient in need thereof appear in further embodiments of the present invention. Also, methods of diagnosing an injury or disease thereby also appear in additional embodiments. Generally, those methods involve the patient gripping the device and raising the device in front of the patient as high as the patient can. Each arm is raised to its unassisted physiological limit, in some cases, which means that the medical professional assisting the patient does not in any way assist. The patient raises each arm until pain, weakness, numbness, or any other perceived limitation arises. Optionally, the patient is told to close her eyes, or wear a blindfold, so that the patient does not attempt to "correct" or influence the measurement. When the patient has complied to the furthest extent possible, the medical professional administering the test observes the angle indicated on the compass by the weighted needle, and also observes whether the needle is favoring the right side or the left side. This angle represents an angular difference in the range of motion of the arms of the patient. The angle can be assigned any desired significance. In some cases, an angle of 5° or less may be considered normal. In other cases, an angle of 10° or more may be considered an indication of injury or disease, or at least of asymmetry. When the angular difference in a range of motion has been measured, a suitable diagnosis may follow. Neurological disorders, such as CVA, ALS, MD, or MS; orthopedic problems, such as rotator cuff, upper extremity fractures, post-surgical recovery issues, cervical or thoracic injuries, arthritis, cartilage degeneration, bone spurs, and other injuries and diseases may be detected or diagnosed in part by employing a method of the present invention. Medical history, medical insurance, Medicare/Medicaid, workman's compensation, disease progression, recovery/rehabilitation progress, ability to perform work-related tasks, ability to perform tasks of daily living, and other purposes may be served by measuring a angular difference in a range of motion in accordance with the present invention.

DETAILED DESCRIPTION OF THE DRAWINGS

Further embodiments of the present invention can be described by reference to the accompanying drawings. The same reference numbers are used to refer to the same components across several figures.

FIG. 1 provides a cartoon of one embodiment of the present invention, device 100, in use. In this figure, left hand 191 of a patient holds the left end 110, and right hand 192 holds the right end 120, of gripping bar 101 of device 100. Weighted needle 130 shows on compass 140 an angular difference of almost 10° favoring left hand 191 of the patient.

Figure 2:
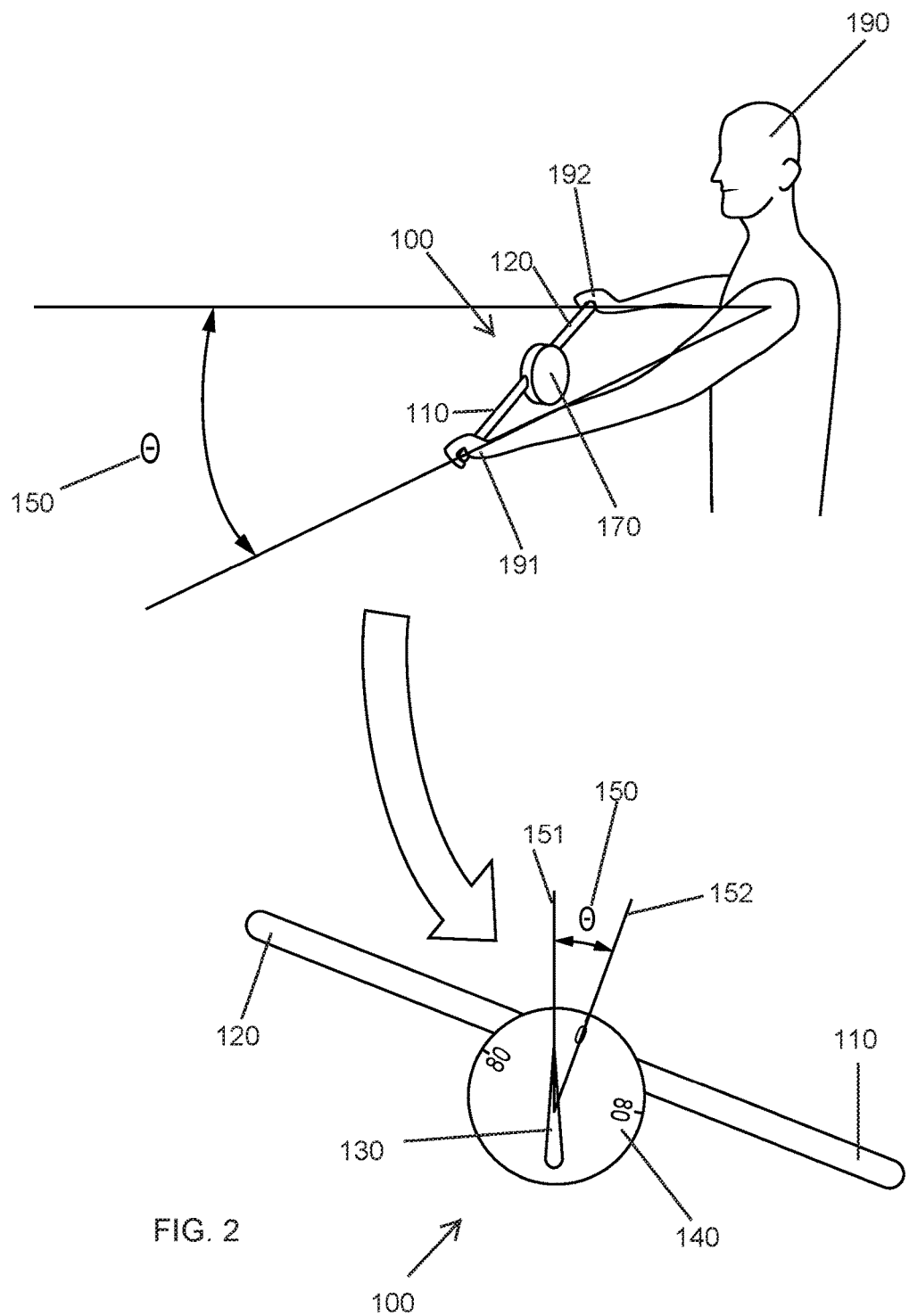
FIG. 2 provides another cartoon illustrating the use of device 100.

FIG. 2 provides another cartoon illustrating the use of device 100. Here we see patient 190 gripping device 100 with right end 120 being in patient's 190 right hand 192, and left end 110 being in patient's 190 left hand 191. Assuming patient 190 has raised both arms to their unassisted physiological limits, there exists an angle Θ 150 that represents an angular difference in a range of motion of the arms of patient 190. Angle Θ 150 is easily displayed on device 100 by weighted needle 130 and compass 140. Weighted needle 130 aligns with absolute vertical axis 151, and compass 140 is aligned with a vertical axis 152 of the housing 170 perpendicular to the gripping bar 101. Here, patient 190 can raise right end 120 higher than left end 110, thereby indicating a greater range of motion in patient's 190 right shoulder versus his left shoulder. A doctor, physical therapist, or other medical professional can read device 100 and record the angle Θ 150 and the direction from the vertical (in this case, to the right) in patient's 190 medical chart, diagnose an injury or disease in patient's 190 left shoulder, and prescribe therapy therefor.

Figure 3:
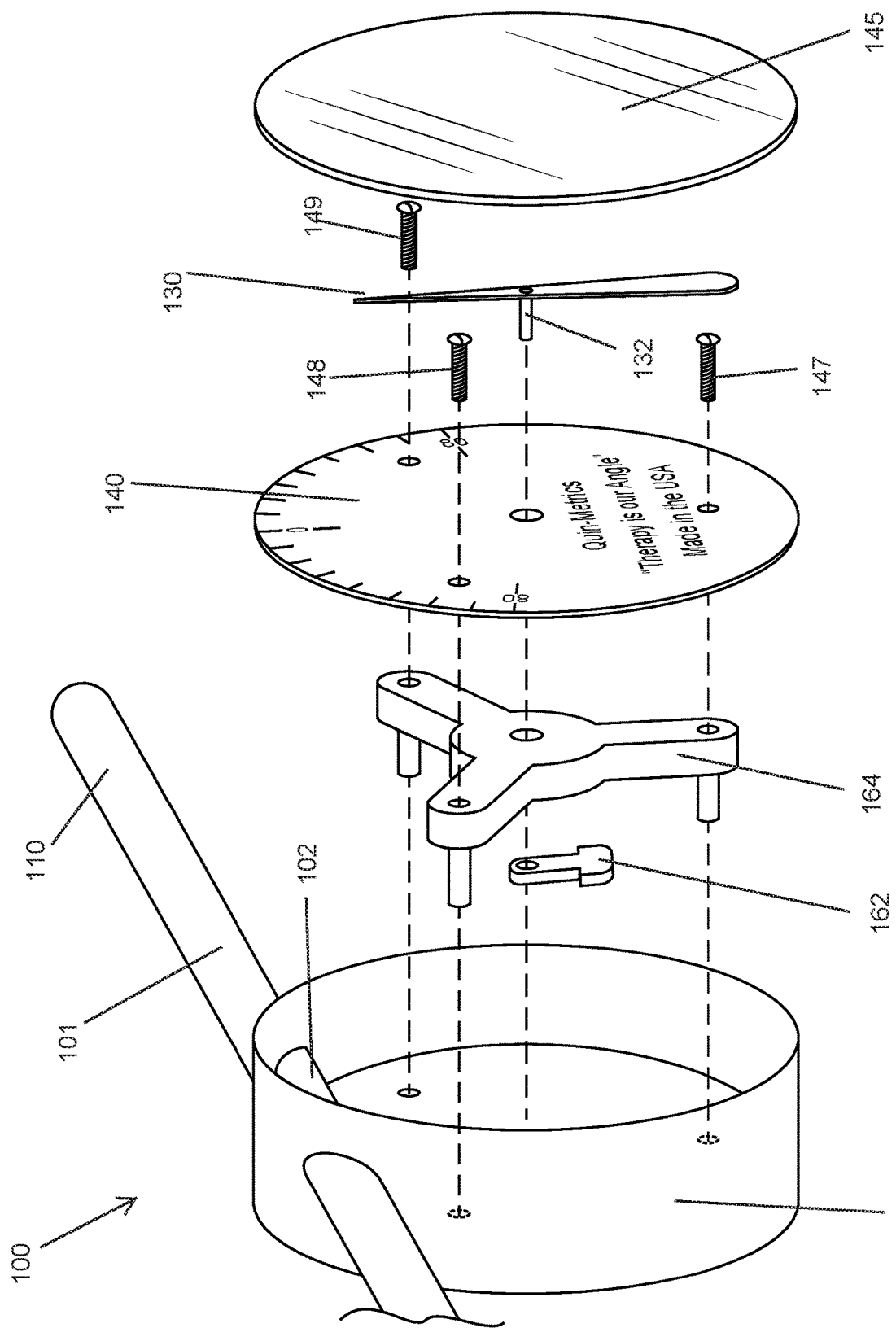
FIG. 3 provides a perspective exploded view showing the components of device 100.

FIG. 3 provides a perspective exploded view showing the components of device 100. Device 100 has gripping bar 101 having midpoint 102 equidistant between left end 110 and right end 120 (not shown). Housing 170 is attached to the gripping bar 101 at the midpoint 102. Weighted needle 130 is configured to point vertically when subjected to the force of gravity. Weighted needle 130 is configured to be rotatably attached to the base 164 by axle 132, and axle 132 also supports weighted pendulum 162. Weighted needle 130, axle 132, compass 140, base 164, and weighted pendulum 162 represent the angle-determining assembly of device 100. That assembly is supported by housing 170 when base 164 is affixed to the housing 170 by screws 147, 148, 149. Watch glass 145 is configured to be affixed to the housing 170, and to protect and enclose the angle-determining assembly. Watch glass 145 can be affixed to housing 170 by any suitable means, such as, for example, adhesive, additional screws (not shown) or the like, and combinations thereof.

Figure 4:
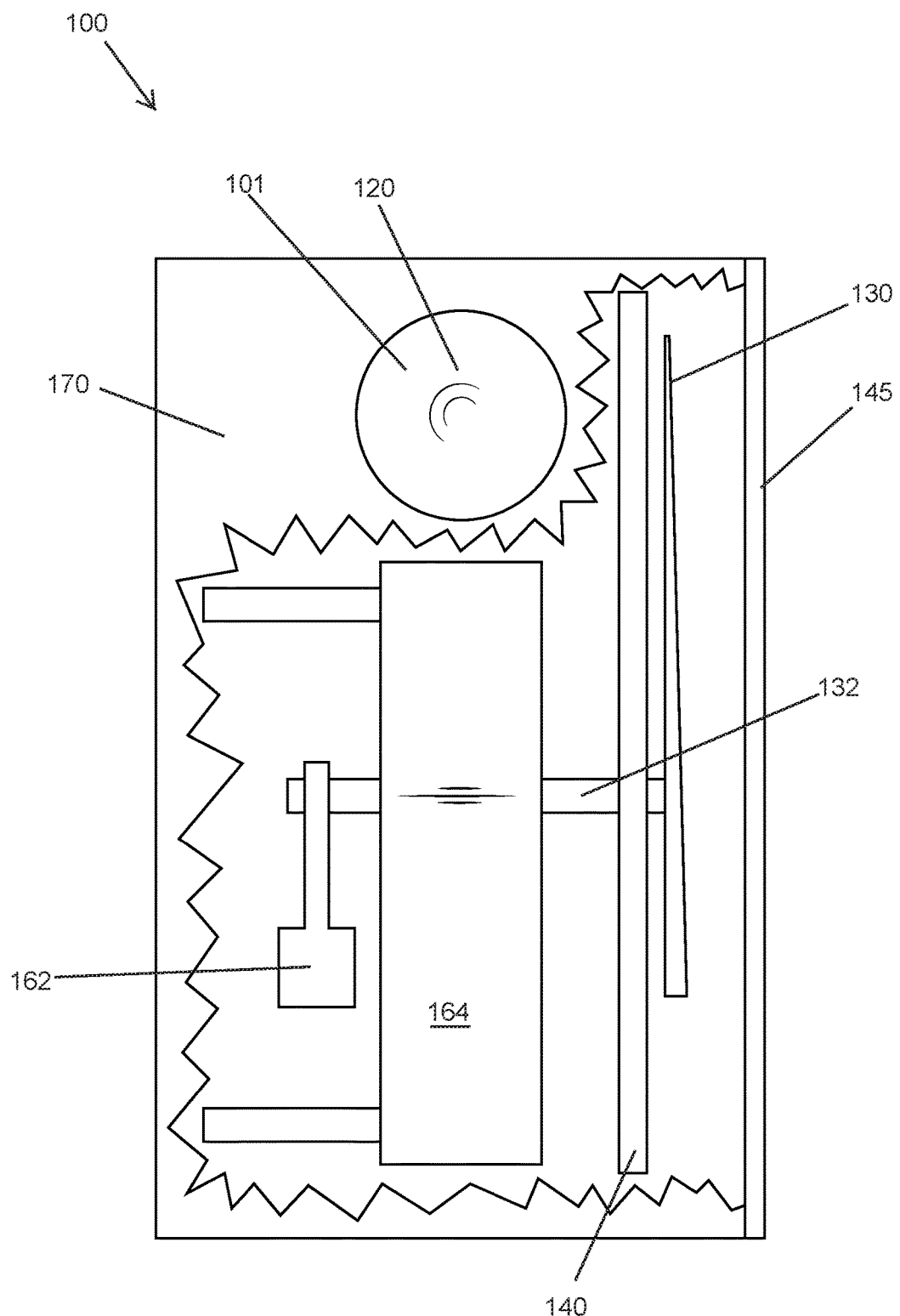
FIG. 4 shows a cut-away right side elevation showing the as-assembled components of device 100.

FIG. 4 shows a cut-away right side elevation showing the as-assembled components of device 100. Here we see weighted needle 130 configured to point vertically when subjected to the force of gravity. Base 164 is affixed to the housing 170, and weighted needle 130 is rotatably attached to base 164 by axle 132. Compass 140 is configured to indicate with weighted needle 130 and angle between an absolute vertical axis 151 (see FIG. 2) and a vertical axis 152 (see FIG. 2) of housing 170 perpendicular to gripping bar 101. Watch glass 145 is affixed to housing 170 with an adhesive.

Figure 5:
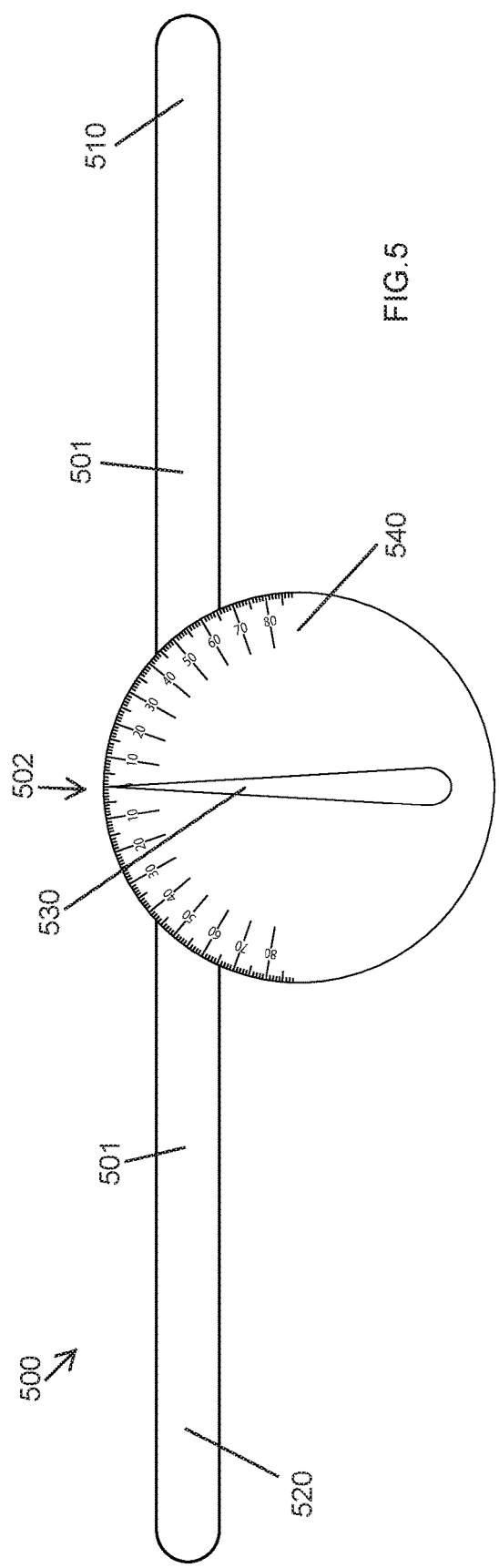
FIG. 5 shows a front elevation view of another embodiment of the present invention, device 500.

FIG. 5 shows a front elevation view of another embodiment of the present invention, device 500. Device 500 comprises gripping bar 501 having a left end 510 and a right end 520 and a midpoint 502 equidistant between the left end 510 and the right end 520. Housing 570 (see FIG. 6) is attached to gripping bar 501 at midpoint 502. Weighted needle 530 is configured to point vertically when subjected to the force of gravity, and is rotatably attached to a base (not visible) inside housing 570 by an axle (not visible). Compass 540 is configured to indicate with weighted needle 530 and angle between an absolute vertical axis and a vertical axis of housing 570 perpendicular to gripping bar 501.

Figure 6:
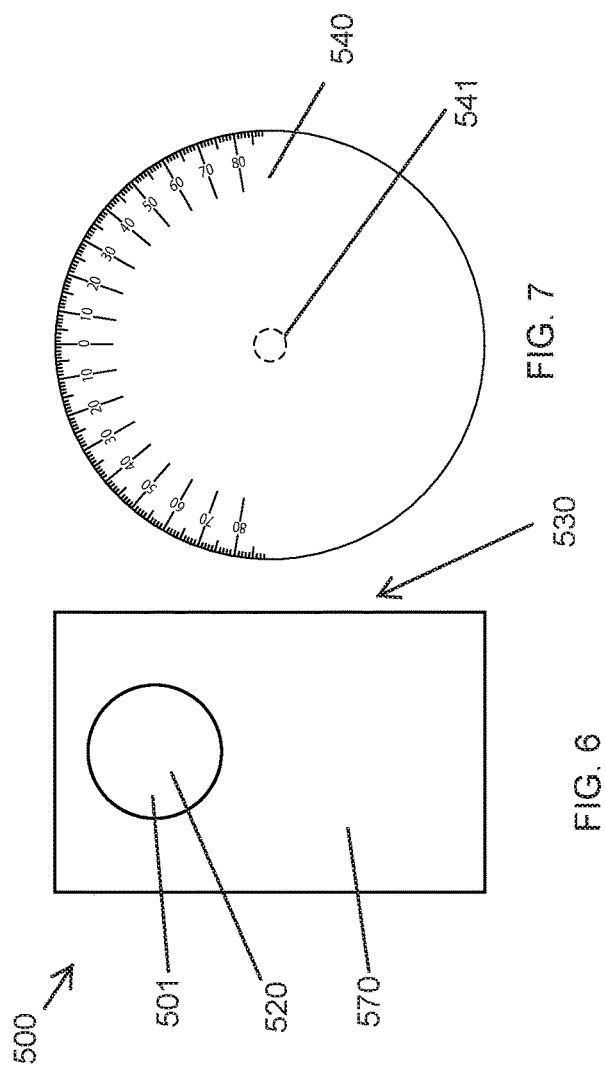
FIG. 6 shows a right side elevation view of device 500.

FIG. 6 shows a right side elevation view of device 500. The front of the device 500 is indicated by reference to weighted needle 530 shown in the figure.

Figure 7:
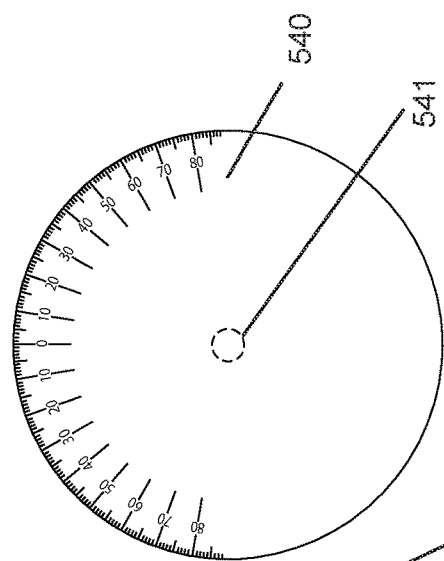
FIG. 7 shows a front elevation view of compass 540 of device 500.

FIG. 7 shows a front elevation view of compass 540 of device 500. For a clear view of the compass 540 without weighted needle 530, compass 540 is shown in this figure. Hole 541 can be any suitable dimension, and allows the mounting of weighted needle 530 on an axle (not shown) that passes through hole 541.

FIG. 8 shows a rear elevation view of device 500. Housing 570 is attached to gripping bar 501 at midpoint 502.

FIG. 9 shows a left side elevation view of device 500. The front of the device 500 is indicated by reference to weighted needle 530 shown in the figure.

Figure 10:
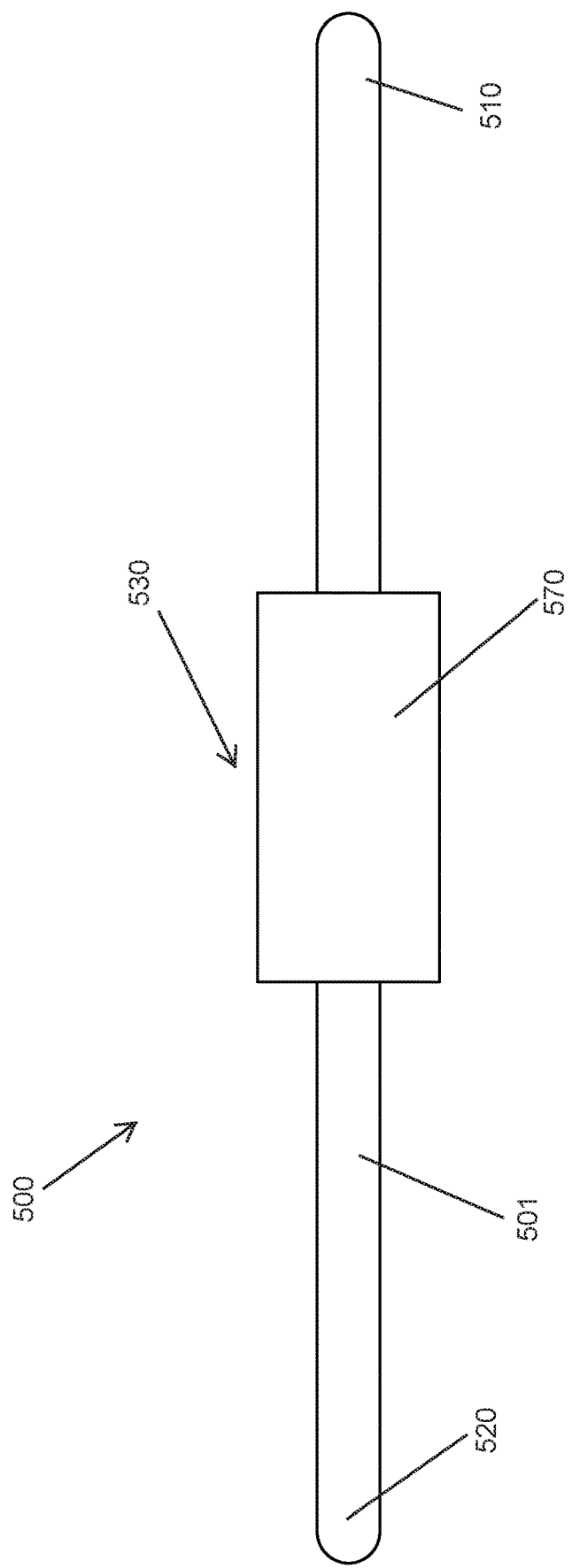
FIG. 10 shows a bottom plan view of device 500.

FIG. 10 shows a bottom plan view of device 500. The front of the device 500 is indicated by reference to weighted needle 530 shown in the figure.

Figure 11:
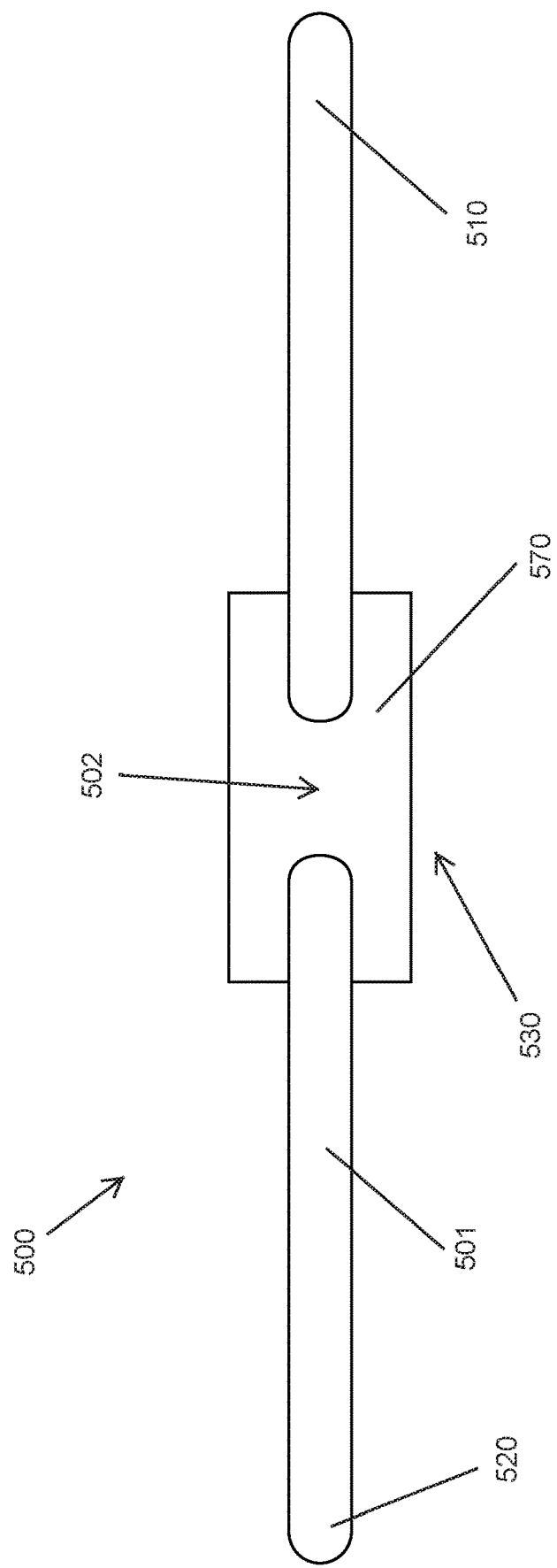
FIG. 11 shows a top plan view of device 500.

FIG. 11 shows a top plan view of device 500. Housing 570 is attached to gripping bar 501 at midpoint 502. The front of the device 500 is indicated by reference to weighted needle 530 shown in the figure.

Figure 12:
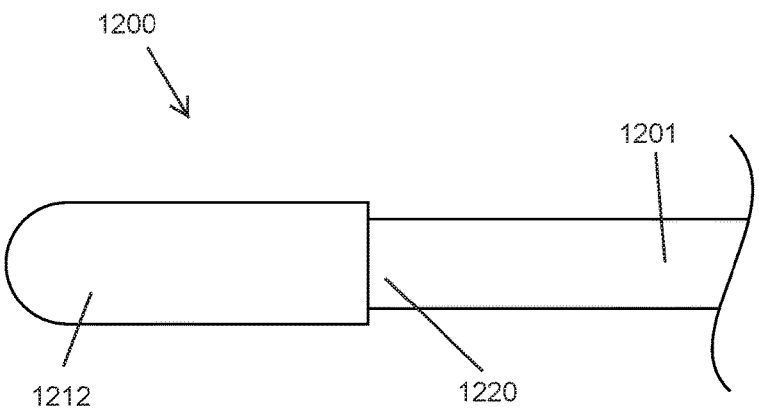
FIG. 12 depicts a foam grip 1212 gripping aid at the right end 1220 of gripping bar 1201 of device 1200 (partial view).

FIG. 12 depicts a foam grip 1212 gripping aid at the right end 1220 of gripping bar 1201 of device 1200 (partial view). Any suitable foam can be used, such as, for example, open cell polymer foam, closed cell polymer foam, natural sponge, and combinations thereof. Synthetic rubber foams such as EPDM rubber foams, neoprene, silicone, and NPVC foams may be mentioned.

Figure 13:
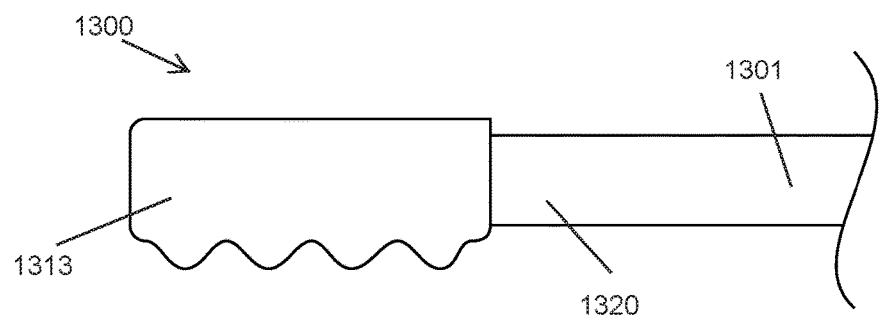
FIG. 13 depicts a handlebar grip 1313 gripping aid at the right end 1320 of gripping bar 1301 of device 1300 (partial view).

FIG. 13 depicts a handlebar grip 1313 gripping aid at the right end 1320 of gripping bar 1301 of device 1300 (partial view). Any suitable material can be used for the handlebar grip 1313, such as, for example, metal, plastic, wood, glass, or a combination thereof. Lightweight plastics appear in some embodiments. Cork also may be mentioned.

Figure 14:
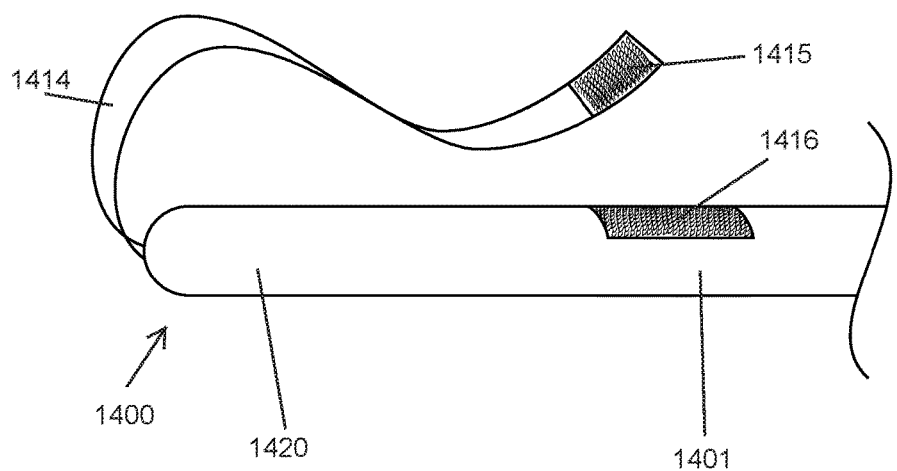
FIG. 14 depicts a strap 1414 gripping aid at the right end 1420 of gripping bar 1401 of device 1400 (partial view).

FIG. 14 depicts a strap 1414 gripping aid at the right end 1420 of gripping bar 1401 of device 1400 (partial view). Any suitable material can be used for the strap 1414, such as, for example, woven material, nonwoven material, natural fibers such as cotton, polymer fibers such as nylon, strips of flexible polymer, and combinations thereof. Patch 1415 and patch 1416 together represent hook-and-loop attachments commonly known as Velcro®. Patch 1415 is attached to the free end of strap 1414, while patch 1416 is attached to gripping bar 1401. Patch 1416 can have any suitable length to accommodate various hand sizes when strap 1414 is affixed about a patient's hand. In some cases, patch 1415 is the softer, loop side, while patch 1416 is the rougher, hook side, to improve the comfort of a patient gripping device 1400.

Figure 15:
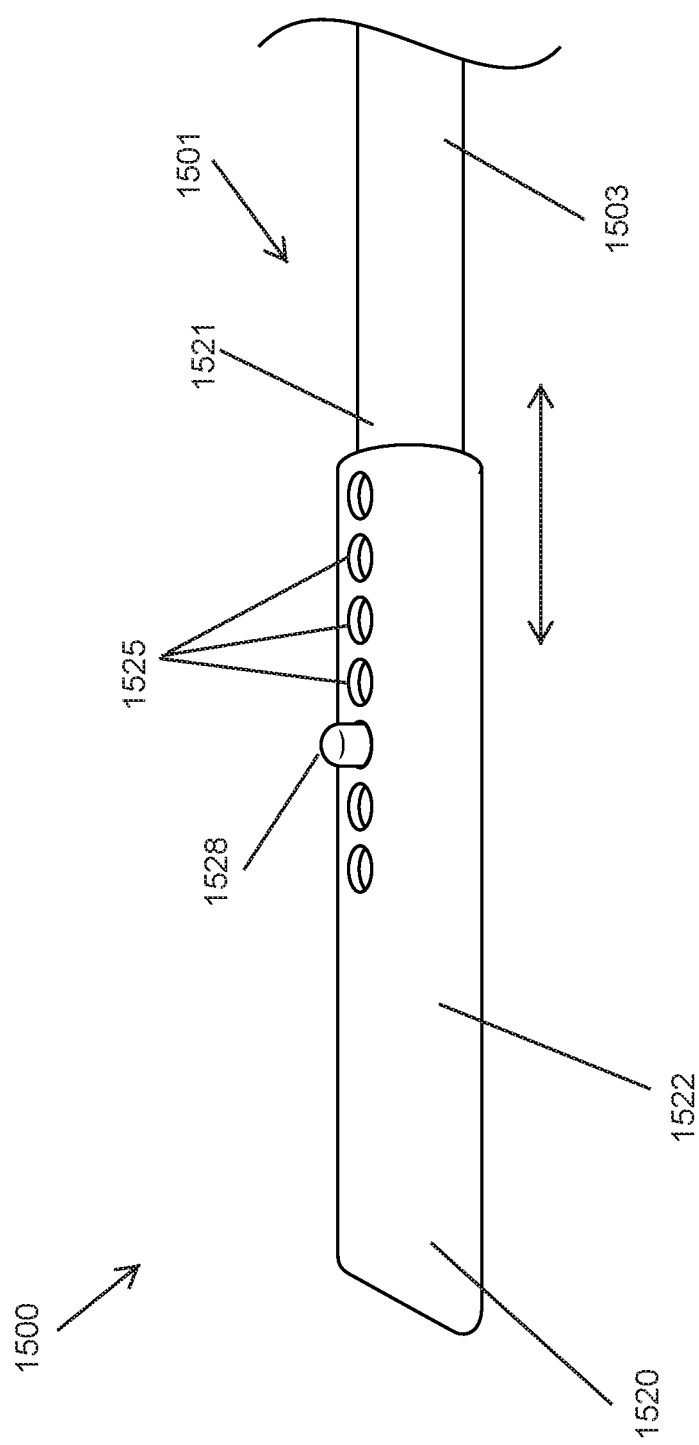
FIG. 15 depicts adjustable-length gripping bar 1501 of device 1500 (partial view).

FIG. 15 depicts adjustable-length gripping bar 1501 of device 1500 (partial view). Gripping bar 1501 has a central portion 1503 that has a right spring-loaded button 1528 on a right side 1521 of central portion 1503. Gripping bar 1501 also has a right hand grip 1522 which comprises the right end 1520 and a right-side series of holes 1525. Right hand grip 1522 is slidably mounted on right side 1521 of central portion 1503. Right spring-loaded button 1528 selectively engages a hole in the right-side series of holes 1525 to adjust the length of gripping bar 1501. Such a gripping bar 1501 optionally has a similar arrangement on its left end (not shown). Adjusting the length of the gripping bar 1501, optionally symmetrically about the midpoint (not shown), allows a medical professional to measure angular differences of motion between the arms of a patient with the hands less than, equal to, or greater than shoulder width apart.

Figure 16:
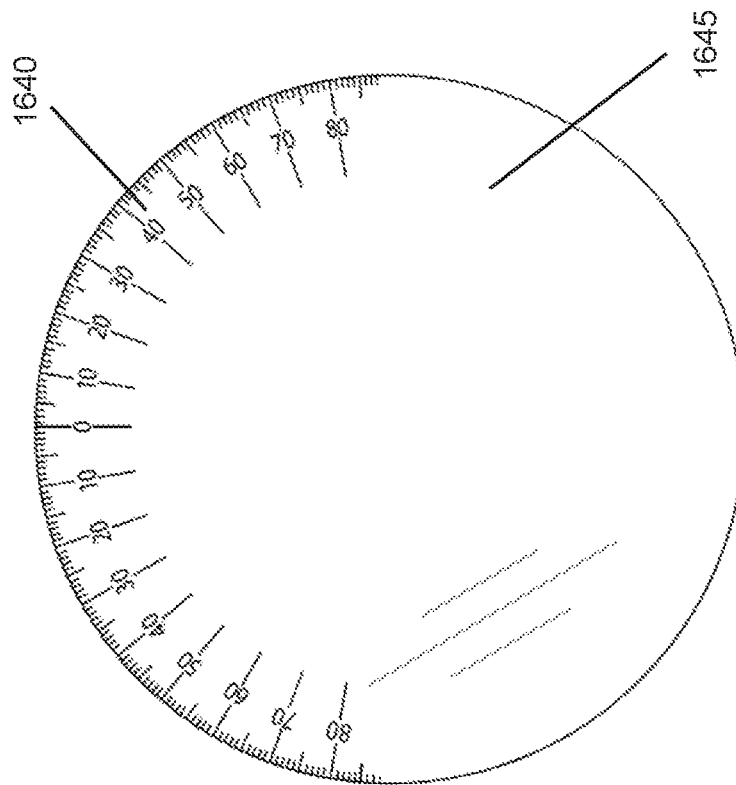
FIG. 16 depicts watch glass 1645 comprising compass 1640.

FIG. 16 depicts watch glass 1645 comprising compass 1640. Such a watch glass 1645 having compass 1640 could replace the watch glass 145 of device 100, and obviate the need for compass 140. Weighted needle 130 would be visible through watch glass 1645, and the angle between weighted needle 130 and compass 1640 could be easily seen.

EXAMPLES

Example 1

Elderly Patient

An 80-year-old woman complaining of shoulder pain and limited left arm mobility is seen by a doctor. In the course of the examination, the doctor has the patient grab the left end and the right end of an inventive device having an angle-determining assembly in her hands. To assist her in holding the device, the doctor secures straps over her hands, which attach to the gripping bar with Velcro® hook-and-loop attachments. The doctor instructs the patient to raise both arms upward as high as she can. With the device attached to her hands assisting her grip thereon, she raises both arms. Her right arm reaches approximately 120° from its resting position by her hip. Her left arm reaches only 110° from its resting position. The doctor observes on the device an angle of 10° to the right of 0° on the compass of the device. The doctor records an angular difference of 10° favoring the right arm on the patient's medical chart, and diagnoses her with mild arthritis in her left shoulder. He prescribes her ibuprofen and a daily regimen of stretching and strengthening exercises for her left arm to improve its range of motion.

Example 2

Injured Athlete

A 20-year-old male patient recovering from a broken right collarbone visits his physical therapist's office. In the course of the examination, the therapist has the patient grab the left end and the right end of an inventive device having an angle-determining assembly in his hands. The therapist instructs the patient to raise both arms upward as high as he can. With the device in his hands, he raises both arms. His left arm reaches 180° from its resting position by his hip; that is, his left arm reaches straight up. His right arm reaches only 120° from its resting position. The therapist observes on the device an angle of 60° to the left of 0° on the compass of the device. The therapist records an angular difference of 60° favoring the left arm on the patient's medical chart, and prescribes the patient a daily regimen of stretching and strengthening exercises for the right arm to improve its range of motion.

Embodiments

Embodiment 1

A device for measuring an angular difference in a range of motion of the arms of a patient in need thereof, the device comprising:
a gripping bar comprising a left end, a right end, and a midpoint equidistant between the left end and the right end;
a housing attached to the gripping bar at the midpoint, and an angle-determining assembly supported by the housing, the assembly comprising
a weighted needle configured to point vertically when subjected to the force of gravity;
a base affixed to the housing, wherein the weighted needle is rotatably attached to the base by an axle; and
a compass configured to indicate with the weighted needle an angle between an absolute vertical axis and a vertical axis of the housing perpendicular to the gripping bar.

Embodiment 2

The device of embodiment 1, wherein the axle supports a weighted pendulum.

Embodiment 3

The device of any one of embodiments 1-2, further comprising a watch glass affixed to the housing, configured to protect and enclose the angle-determining assembly.

Embodiment 4

The device of any one of embodiments 1-2, wherein the compass is present on a watch glass affixed to the housing.

Embodiment 5

The device of any one of embodiments 1-4, wherein the housing comprises metal, plastic, wood, glass, or a combination thereof.

Embodiment 6

The device of any one of embodiments 1-5, wherein the gripping bar comprises metal, plastic, wood, glass, or a combination thereof.

Embodiment 7

The device of any one of embodiments 1-6, wherein the weighted needle comprises metal, plastic, wood, glass, or a combination thereof.

Embodiment 8

The device of embodiment 7, wherein the weighted needle is metal.

Embodiment 9

The device of any one of embodiments 2-8, wherein the weighted pendulum comprises metal, plastic, wood, glass, or a combination thereof.

Embodiment 10

The device of embodiment 9, wherein the weighted pendulum is metal.

Embodiment 11

The device of any one of embodiments 1-10, wherein the gripping bar is at least one foot long.

Embodiment 12

The device of any one of embodiments 1-11, wherein the gripping bar is no more than three feet long.

Embodiment 13

The device of any one of embodiments 1-12, further comprising at least one weight.

Embodiment 14

The device of embodiment 13, wherein the at least one weight is no more than one pound, no more than three pounds, no more than five pounds, no more than ten pounds, or more than ten pounds.

Embodiment 15

The device of any one of embodiments 1-14, wherein the gripping bar comprises at least one mechanism for adjusting the length of the gripping bar.

Embodiment 16

The device of embodiment 15, wherein the at least one mechanism for adjusting the length of the gripping bar comprises
a spring-loaded button on a first portion of the gripping bar, and
a series of holes on a second portion of the gripping bar slidably mounted on the first portion, the series of holes positioned so that the spring-loaded button can selectively engages any one hole in the series of holes, thereby adjusting the length of the gripping bar.

Embodiment 17

The device of any one of embodiments 1-14, wherein the gripping bar comprises
a central portion comprising the midpoint and the housing attached at the midpoint, further comprising a left side opposite a right side about the midpoint, a left spring-loaded button on the left side and a right spring-loaded button on the right side;
a left hand grip comprising the left end and a left-side series of holes, the left hand grip being slidably mounted on the left side of the central portion so that the left spring-loaded button selectively engages any hole in the left-side series of holes to adjust the length of the gripping bar; and
a right hand grip comprising the right end and a right-side series of holes, the right hand grip being slidably mounted on the right side of the central portion so that the right spring-loaded button selectively engages any hole in the right-side series of holes to adjust the length of the gripping bar.

Embodiment 18

The device of any one of embodiments 1-17, wherein the gripping bar further comprises, at the left end and the right end, one or more substantially similar gripping aids.

Embodiment 19

The device of embodiment 18, wherein the one or more substantially similar gripping aids are chosen from foam grips, handlebar grips, and straps.

Embodiment 20

The device of embodiment 19, wherein the one or more substantially similar gripping aids comprise straps.

Embodiment 21

The device of embodiment 20, wherein the straps comprise hook-and-loop attachments.

Embodiment 22

A method of measuring an angular difference in a range of motion of the arms of a patient in need thereof, comprising:
obtaining the device of any one of embodiments 1-21;
having the patient grip the left end in the patient's left hand and the right end in the patient's right hand;
having the patient raise both arms to both arms' unassisted physiological limits; and
observing on the compass with the weighted needle the angle, wherein the angle represents the angular difference in the range of motion of the arms of the patient.

Embodiment 23

A method of diagnosing an injury or disease in a patient in need thereof, comprising:
obtaining the device of any one of embodiments 1-21;
having the patient grip the left end in the patient's left hand and the right end in the patient's right hand;
having the patient raise both arms to both arms' unassisted physiological limits;
observing on the compass with the weighted needle the angle, wherein the angle is equal to or greater than 10°.

Embodiment 24

A method of measuring an angular difference in a range of motion of the arms of a patient in need thereof, comprising:
obtaining the device of any one of embodiments 20-21;
affixing the left end to the patient's left hand and the right end to the patient's right hand with the straps;
having the patient raise both arms to both arms' unassisted physiological limits; and
observing on the compass with the weighted needle the angle, wherein the angle represents the angular difference in the range of motion of the arms of the patient.

Embodiment 25

A method of diagnosing an injury or disease in a patient in need thereof, comprising:
obtaining the device of any one of embodiments 20-21;
affixing the left end to the patient's left hand and the right end to the patient's right hand with the straps;
having the patient raise both arms to both arms' unassisted physiological limits;

observing on the compass an angle between the absolute vertical axis and the vertical axis of the housing perpendicular to the gripping bar, wherein the angle is equal to or greater than 10°.

Embodiment 26

A method of diagnosing an injury or disease in a patient in need thereof, comprising:
measuring an angular difference in a range of motion in the arms of the patient, thereby diagnosing the injury or disease.

Embodiment 27

The method of embodiment 26, wherein the measuring is performed by the patient raising the patient's arms to their unassisted physiological limits.

Embodiment 28

The method of embodiment 27, wherein the raising is performed with the patient's hands being shoulder width apart.

Embodiment 29

The method of embodiment 27, wherein the raising is performed with the patient's hands being less than shoulder width apart.

Embodiment 30

The method of embodiment 27, wherein the raising is performed with the patient's hands being greater than shoulder width apart.

Embodiment 31

The method of any one of embodiments 27-30, wherein the raising is performed against an increasing force.

Embodiment 32

The method of any one of embodiments 27-30, wherein the raising is performed against a weight.

Embodiment 33

The method of embodiment 32, wherein the weight is no more than one pound, no more than three pounds, no more than five pounds, no more than ten pounds, or more than ten pounds.

Embodiment 34

A method of treating an injury or disease in a patient in need thereof, wherein the injury or disease manifests an angular difference in a range of motion of the arms of the patient, the method comprising:
obtaining the device of any one of embodiments 1-21;
having the patient grip the left end in the patient's left hand and the right end in the patient's right hand;
having the patient raise both arms to both arms' unassisted physiological limits;
observing on the compass with the weighted needle the angle, wherein the angle represents the angular difference in the range of motion of the arms of the patient; and
repeating having the patient grip the device and having the patient raise both arms, for the purpose of detecting a decrease in the angular difference in the range of motion.

Embodiment 35

The method of embodiment 34, further comprising administering to the patient at least one analgesic compound suitable for managing pain while having the patient raise both arms to both arms' unassisted physiological limits.

Embodiment 36

The method of embodiment 35, wherein the at least one analgesic compound is chosen from ibuprofen, aspirin, acetaminophen, hydrocodone, oxycodone and combinations thereof.

Embodiment 37

The method of any one of embodiments 34-36, further comprising administering to the patient at least one steroid via intramuscular injection.

Embodiment 38

The method of any one of embodiments 34-37, further comprising having the patient perform at least one stretching movement before or after having the patient raise both arms to both arms' unassisted physiological limits.

As previously stated, detailed embodiments of the present invention are disclosed herein; however, it is to be understood that the disclosed embodiments are merely exemplary of the invention that may be embodied in various forms. It will be appreciated that many modifications and other variations stand within the intended scope of this invention as claimed below. Furthermore, the foregoing description of various embodiments does not necessarily imply exclusion. For example, "some" embodiments may include all or part of "other" and "further" embodiments within the scope of this invention. In addition, "a" does not mean "one and only one;" "a" can mean "one and more than one."

I claim:

1. A method of measuring an angular difference in a range of motion of the arms of a patient in need thereof, comprising:
obtaining a device comprising:
a gripping bar comprising a left end, a right end, and a midpoint equidistant between the left end and the right end;
a housing attached to the gripping bar at the midpoint, and an angle-determining assembly supported by the housing, the angle-determining assembly comprising
a weighted needle configured to point vertically when subjected to the force of gravity;
a base affixed to the housing, wherein the weighted needle is rotatably attached to the base by an axle; and
a compass configured to indicate with the weighted needle an angle between an absolute vertical axis and a vertical axis of the housing perpendicular to the gripping bar;
having the patient wear a blindfold;
having the patient grip the left end in the patient's left hand palm facing down and the right end in the patient's right hand palm facing down;

having the patient raise both arms to both arms' unassisted physiological limits;
observing on the compass the angle indicated by the weighted needle,
wherein the angle represents the angular difference in the range of motion of the arms of the patient; and,
diagnosing the patient with an injury, disease, or asymmetry when the angle is 10° or more.

2. The method of claim 1, wherein the axle supports a weighted pendulum and the weighted needle.

3. The method of claim 1, wherein the weighted needle is metal.

4. The method of claim 2, wherein the weighted pendulum is metal.

5. The method of claim 1, wherein the device comprises at least one weight.

6. The method of claim 1, wherein the gripping bar comprises
   a central portion comprising the midpoint and the housing attached at the midpoint, further comprising a left side opposite a right side about the midpoint, a left spring-loaded button on the left side and a right spring-loaded button on the right side;
   a left hand grip comprising the left end and a left-side series of holes, the left hand grip being slidably mounted on the left side of the central portion so that the left spring-loaded button selectively engages any hole in the left-side series of holes to adjust the length of the gripping bar; and
   a right hand grip comprising the right end and a right-side series of holes, the right hand grip being slidably mounted on the right side of the central portion so that the right spring-loaded button selectively engages any hole in the right-side series of holes to adjust the length of the gripping bar.

7. The method of claim 1, wherein the gripping bar further comprises, at the left end and the right end, one or more gripping aids chosen from foam grips and handlebar grips.

8. The method of claim 1, wherein the gripping bar further comprises, at the left end and the right end, one or more gripping aids which are straps,
   wherein the method further comprises affixing the left end to the patient's left hand and the right end to the patient's right hand with the straps, before having the patient raise both arms.

9. The method of claim 8, wherein the straps comprise hook-and-loop attachments.

\* \* \* \* \*